US011439513B2

(12) United States Patent
Lefebvre et al.

(10) Patent No.: US 11,439,513 B2
(45) Date of Patent: Sep. 13, 2022

(54) GLENOID IMPLANT FOR INVERTED SHOULDER PROSTHESIS

(71) Applicant: SHOULDER FRIENDS INSTITUTE, Paris (FR)

(72) Inventors: Yves Lefebvre, Strasbourg (FR); Stephane Audebert, Blecourt (FR); Johannes Barth, Meylan (FR); Christophe Charousset, Paris (FR); Jerome Garret, Limonest (FR); Arnaud Godeneche, Saint Cyr au Mont d'Or (FR); Jacques Guery, Nevers (FR); Thierry Joudet, Libourne (FR); David Gallinet, Geneuille (FR)

(73) Assignee: SHOULDER FRIENDS INSTITUTE, Paris (FR)

( * ) Notice: Subject to any disclaimer, the term of this patent is extended or adjusted under 35 U.S.C. 154(b) by 0 days.

(21) Appl. No.: 16/885,979

(22) Filed: May 28, 2020

(65) Prior Publication Data
US 2020/0289282 A1    Sep. 17, 2020

Related U.S. Application Data

(63) Continuation of application No. PCT/FR2018/052996, filed on Nov. 27, 2018.

(30) Foreign Application Priority Data

Nov. 28, 2017  (FR) ...................................... 17/61301

(51) Int. Cl.
*A61F 2/40*  (2006.01)
*A61F 2/30*  (2006.01)

(52) U.S. Cl.
CPC .... *A61F 2/4081* (2013.01); *A61F 2002/3041* (2013.01); *A61F 2002/3065* (2013.01);
(Continued)

(58) Field of Classification Search
CPC .. A61F 2/4081; A61F 2002/4085; A61F 2/32; A61F 2/36; A61F 2002/30245;
(Continued)

(56) References Cited

U.S. PATENT DOCUMENTS

2004/0220673 A1 * 11/2004 Pria ....................... A61F 2/4081
                                                              623/19.12
2015/0305877 A1 * 10/2015 Gargac .................. A61F 2/4081
                                                              623/19.11

FOREIGN PATENT DOCUMENTS

| EP | 1332734    | 8/2003 |
|----|------------|--------|
| EP | 2601912    | 6/2013 |
| WO | 2015103090 | 7/2015 |

OTHER PUBLICATIONS

International Search Report for International Application PCT/FR2018/052996, dated Apr. 16, 2019.

* cited by examiner

*Primary Examiner* — Christopher D. Prone
(74) *Attorney, Agent, or Firm* — Burris Law, PLLC

(57) ABSTRACT

A glenoid implant for an inverted shoulder prosthesis includes a base, a glenosphere having a central orifice and mounted on the base by mutual wedging between conical bearing surfaces, a main anchoring screw crossing the base and including an anchor rod having a tapped end segment, and an inner hole having a threaded intermediate portion, and a tip portion. A locking screw crosses the central orifice and includes a proximal head and a locking rod having an end segment intended to slide in the tip portion of the inner hole and a tapped intermediate segment intended to cooperate by screwing with the intermediate portion of the inner hole to lock the mutual wedging of the conical bearing surfaces, the proximal head abutting on an annular bearing surface in the central orifice.

12 Claims, 10 Drawing Sheets

(52) U.S. Cl.
CPC ........... *A61F 2002/30245* (2013.01); *A61F 2002/30332* (2013.01); *A61F 2002/30433* (2013.01); *A61F 2002/30772* (2013.01); *A61F 2002/4085* (2013.01)

(58) Field of Classification Search
CPC .... A61F 2002/30332; A61F 2002/3041; A61F 2002/30433; A61F 2002/3065; A61F 2002/30772
See application file for complete search history.

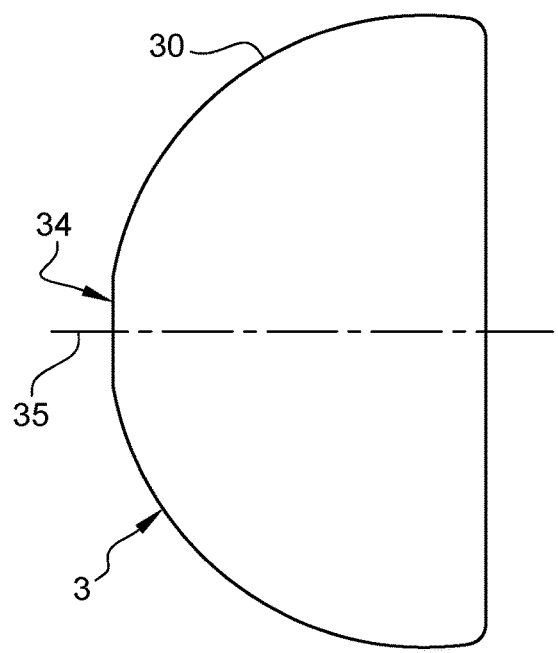
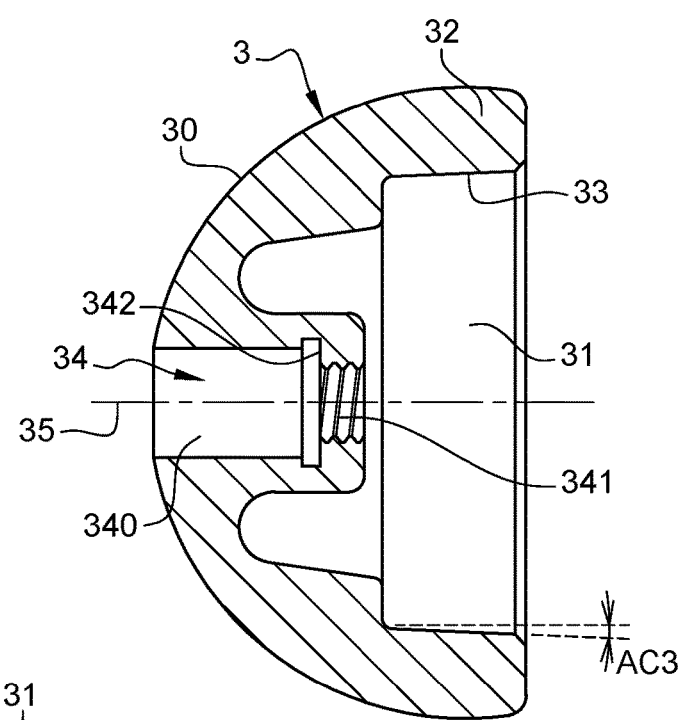
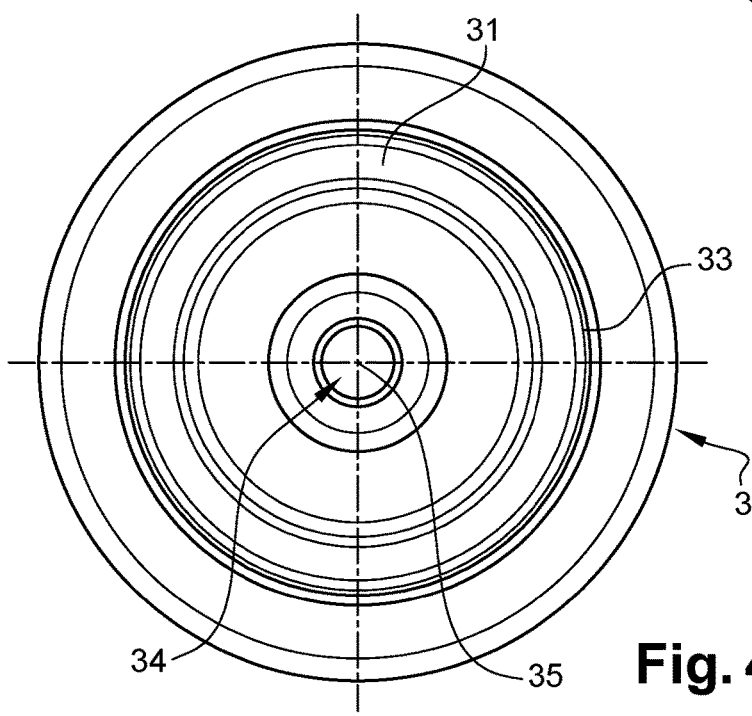

GLENOID IMPLANT FOR INVERTED SHOULDER PROSTHESIS

CROSS-REFERENCE TO RELATED APPLICATIONS

This application is a continuation of International Application No. PCT/FR2018/052996, filed on Nov. 27, 2018, which claims priority to and the benefit of FR 17/61301, filed on Nov. 28, 2017. The disclosures of the above applications are incorporated herein by reference.

FIELD

The present disclosure relates to a glenoid implant for an inverted shoulder prosthesis.

BACKGROUND

The statements in this section merely provide background information related to the present disclosure and may not constitute prior art.

Conventionally, a glenoid implant comprises a base intended to be anchored on a glenoid cavity of a scapula, and a glenosphere mounted on the base and defining a convex articulation surface formed as a spherical portion.

It is known, in particular from the document EP 2 601 912 to provide a mounting of the glenosphere on the base by a mutual wedging between female and male conical bearing surfaces, and to provide a main anchoring screw crossing the base and shaped for anchorage of the base on the glenoid cavity. However, the glenoid implant of this document EP 2 601 912 has the drawback that no locking of the glenosphere on the base is provided for.

To partially solve this drawback, the international application WO 2015/103090 proposes, in addition to a mutual wedging between conical bearing surfaces, using a locking screw crossing the glenosphere to lock the latter on the base. In this document, a main anchoring screw is fitted therebeneath (on the side of the inner face of the base intended to be in contact with the prepared native glenoid surface) so as to be blocked on the base by a circlip or by a proximal tapping having a left pitch whereas the distal tapping serving for anchorage into the glenoid cavity has a right pitch, and furthermore the locking screw is screwed into the base.

However, the glenoid implant of this document WO 2015/103090 has a first drawback which is the absence of guidance of the glenosphere during the positioning thereof on the base, and a second drawback which consists in that the compressive forces in the main anchoring screw pass through the circlip or through the proximal tapping, thereby altering the overall mechanical strength of the glenoid implant.

The state of the art may also be illustrated by the teaching of the document EP 1 332 734 which discloses a glenoid implant comprising a base provided with a fixed anchor stud for anchorage into the glenoid cavity, and a glenosphere mounted on the base by a mutual wedging between female and male conical bearing surfaces. There is also provided a locking screw to lock the glenosphere on the base in a locked position. First, the locking screw is hooked by the bottom on the glenosphere by means of an upper tapping screwed into a threaded orifice of the glenosphere and an intermediate tapping screwed into a bushing which, in turn, is screwed on the bottom of the glenosphere. By these three simultaneous screwings, it is obvious that such a solution is tricky to make, because it requires a very high accuracy for all screwings coinciding simultaneously. Afterwards, the locking screw is screwed until the upper tapping leaves the threaded orifice in the glenosphere, and the intermediate screwing leaves the bushing so as to be screwed into a threading provided in the fixed anchor stud. Such a glenoid implant has the drawback that anchorage is not achieved by a fixed anchor stud, and therefore without screwing, and also the drawbacks of complexity and additional cost related to the use of an intermediate part which is the bushing.

It is also known from U.S. Patent Publication No. 2004/0220673 to use a glenoid implant comprising a base anchored into the glenoid cavity by means of an anchoring screw and a glenosphere mounted on the base by a mutual wedging between female and male conical bearing surfaces and locked on the base by means of a locking screw which is screwed into the anchoring screw. During mounting of the glenosphere on the base, this glenosphere is indexed by means of the head of the anchoring screw which is conical and which cooperates with a centering hole provided at the center of the glenosphere. A drawback of this glenoid implant consists in that the head of the anchoring screw must project on the top of the base sufficiently to allow guiding the glenosphere, and this projection may be troublesome for the surgeon during additional operations to be performed prior to the set-up of the glenosphere on the base, such as for example during screwing of anchor peripheral screws into the glenoid cavity.

SUMMARY

This section provides a general summary of the disclosure and is not a comprehensive disclosure of its full scope or all of its features.

The present disclosure provides a glenoid implant which enable guidance and locking of the glenosphere on the base, while providing an improved mechanical strength.

The present disclosure also aims at providing a glenoid implant shaped so as not to hinder additional operations to be performed prior to locking of the glenosphere on the base.

To this end, it provides a glenoid implant for an inverted shoulder prosthesis, comprising:

a base intended to be anchored on a glenoid cavity of a scapula and having a main orifice crossing the base;

a glenosphere defining a convex articulation surface formed in a spherical portion and having a central orifice crossing the glenosphere, wherein said glenosphere is mounted on said base by mutual wedging between female and male conical bearing surfaces provided on the glenosphere and on the base;

a main anchoring screw crossing the main orifice of said base and shaped for anchorage of the base on the glenoid cavity, wherein said main anchoring screw comprises a main head and an anchor rod having an end segment provided with an external tapping; and a locking screw, coaxial with the main anchoring screw, crossing the central orifice of the glenosphere to lock the glenosphere on the base in a locked position, wherein said locking screw comprises a proximal head and a locking rod having an intermediate segment provided with an external tapping and extended by an end segment;

wherein said glenoid implant is remarkable in that:

the main anchoring screw has an inner hole opening into the main head and having successively, starting from the main head and in the direction of the end segment of its anchor rod, an inlet portion shaped so as to cooperate with a screwing tool, an intermediate portion provided with a threading and a tip portion; and the locking rod has its end segment which has a length longer than a cumulated length of the inlet portion and of the intermediate portion of the inner hole of the main anchoring screw, so that said end segment of the locking rod is intended to slide inside the tip portion of the inner hole of the main anchoring screw to center the conical bearing surfaces relative to one another, and the intermediate segment of the locking rod is intended to cooperate afterwards by screwing with the intermediate portion of the inner hole of the main anchoring screw to lock the mutual wedging of the conical bearing surfaces, the proximal head of the locking screw abutting on an annular bearing surface provided inside the central orifice of the glenosphere.

Thus, the locking screw provides both guidance of the glenosphere on the base in order to guide the two conical bearing surfaces in mutual and centered contact, and locking of the glenosphere on the base with a transmission of the compressive forces which pass through the central anchoring screw and also through the locking screw and through the annular bearing surface provided inside the central orifice of the glenosphere thereby providing enhanced mechanical strength in comparison with the prior art.

Thanks to the present disclosure, the guidance of the glenosphere will allow facilitating the work of the surgeon, who sometimes works bearing on retractors depending on the retained access to the articulation which depends on the surgical approach.

Throughout the entire description, the lengths are measured along the longitudinal and coaxial axes of the main anchoring screw and of the locking screw, when in place and in the locked position.

According to one feature, the central orifice of the glenosphere has successively, starting from the convex articulation surface in the direction of the base, a proximal portion shaped so as to completely receive the proximal head of the locking screw, and a distal portion provided with a threading complementary to the external tapping of the intermediate segment of the locking rod of the locking screw, wherein the annular bearing surface of the central orifice of the glenosphere is provided at the interface between said proximal portion and said distal portion.

Thus, the locking screw may be positioned beforehand on the glenosphere, by making the intermediate segment of the locking rod of the locking screw pass by screwing through the threaded distal portion of the central orifice of the glenosphere, thereby blocking sliding of the locking screw upwards (blocking with the threaded distal portion) and downwards (blocking with the annular bearing surface).

Advantageously, the distal portion of the central orifice of the glenosphere has a length smaller than that of the intermediate segment of the locking rod of the locking screw.

According to another feature, the locking rod of the locking screw has a proximal segment extending between the proximal head and the intermediate segment.

This intermediate segment contributes to authorizing a degree of sliding of the locking screw so as to facilitate mounting and to enable the impingement of the glenosphere for mounting by mutual wedging between the female and male conical bearing surfaces.

Advantageously, the threaded distal portion of the central orifice of the glenosphere has a length smaller than that of the proximal segment of the locking rod of the locking screw.

In one particular form, the main anchoring screw and the locking screw are coaxial with the male and female conical bearing surfaces.

In another particular form, in the locked position, the main head of the main anchoring screw abuts on an annular bearing surface provided inside the main orifice of the base, thereby promoting a transmission of the compressed forces in the main anchoring screw via this annular bearing surface.

According to a possibility of the present disclosure, the main head of the main anchoring screw has an external tapping, and the main orifice of the base has an inlet portion opening onto an outer face of the base opposite the glenosphere, wherein said inlet portion is provided with a threading complementary to said external tapping of said main head, so that said main head is screwed into said inlet portion.

According to another possibility of the present disclosure, the external tapping of the main head of the main anchoring screw has a tapping pitch smaller than that of the external tapping of the end segment of the anchor rod, which allows improving the anchorage of the external tapping of the end segment of the anchor rod by screwing into the glenoid cavity.

Thus, the external tapping of the end segment of the anchor rod has a large tapping pitch adapted for hooking in cancellous bone, whereas the external tapping of the main head of the main anchoring screw has a small tapping pitch (such as a metric pitch), so that each screw revolution does not corresponds to the same screwing length for these two tappings.

In accordance with another advantageous feature of the present disclosure, the base has a central stud projecting from an inner face opposite to the glenosphere, wherein said central stud is hollow and is crossed by the main orifice and the main anchoring screw whose end segment of the anchor rod projects beyond said central stud; such a hollow stud being advantageous to promote anchorage into the glenoid cavity and enable centering of the main anchoring screw so as to provide coaxiality with the locking screw.

Advantageously, the main orifice of the base has an outlet portion which extends the inlet portion and which crosses the central stud, and the anchor rod has an intermediate segment shaped so as to be slidably and tightly mounted inside the outlet portion of the main orifice of the base, thereby providing centering of the main anchoring screw and therefore coaxiality with the locking screw.

The present disclosure also concerns the feature according to which the glenoid implant further comprises several secondary anchoring screws shaped for anchorage of the base on the glenoid cavity, wherein said secondary anchoring screws cross the base and are disposed at the periphery around the main anchoring screw.

Such peripheral anchoring screws are intended to complete and reinforce anchorage into the glenoid cavity.

According to one possibility, the main head of the main anchoring screw does not project beyond an outer face opposite the glenosphere.

Thus, the main anchoring screw does not project outwardly from the base and therefore does not hinder the additional operations to be performed prior to locking of the glenosphere on the base, such as for example the operations of screwing the above-described secondary anchoring screws.

The present disclosure also relates to an inverted shoulder prosthesis comprising a glenoid implant in accordance with the present disclosure, and a humeral implant intended to be anchored on a humerus and comprising a hemispherical cap defining a concave articulation surface shaped for articulation with the convex articulation surface of the glenosphere of the glenoid implant.

The present disclosure finds application in a method for using a glenoid implant in accordance with the present disclosure, comprising the following steps of:

fitting the main anchor spring into the main orifice of the base;

fitting the locking screw into the central orifice of the glenosphere until the end segment of the locking rod projects beyond the glenosphere;

approaching the glenosphere of the base so that the end segment of the locking rod slides inside the tip portion of the inner hole of the main anchoring screw and the conical bearings surfaces comes into contact with one another;

pushing in and screwing the locking rod so that the intermediate segment of the locking rod cooperates by screwing with the intermediate portion of the inner hole of the main anchoring screw to lock the mutual wedging of the conical bearing surfaces, the proximal head of the locking screw abutting on the annular bearing surface provided inside the central orifice of the glenosphere.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which:

FIG. 2 is a side view of the glenosphere of the glenoid implant of FIG. 1;

FIG. 3 is a cross-sectional view of the glenoid implant of FIG. 1;

FIG. 4 is a bottom view of the glenosphere of the glenoid implant of FIG. 1;

Figure 1:
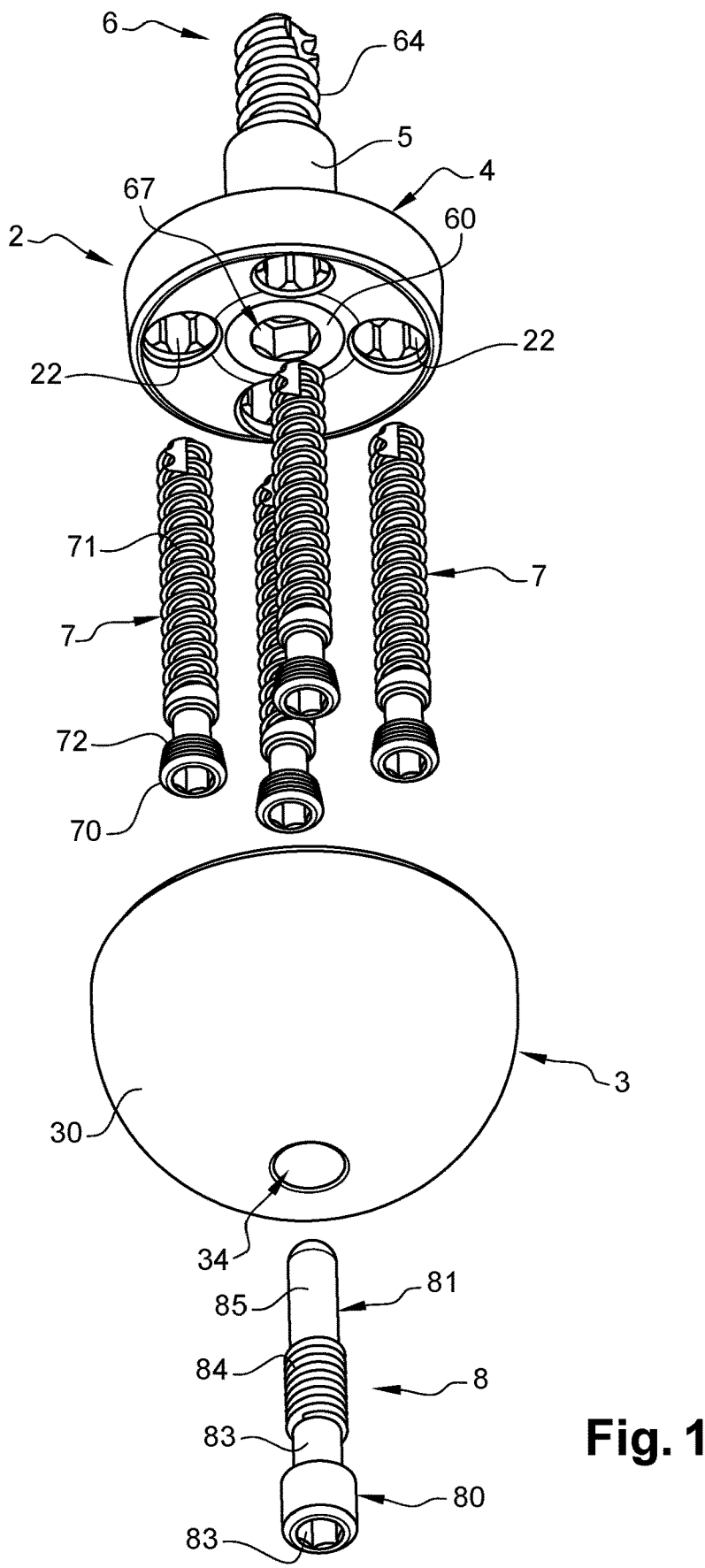
FIG. 1 is a schematic exploded perspective view of a glenoid implant before mounting according to the present disclosure.
Figure 5:
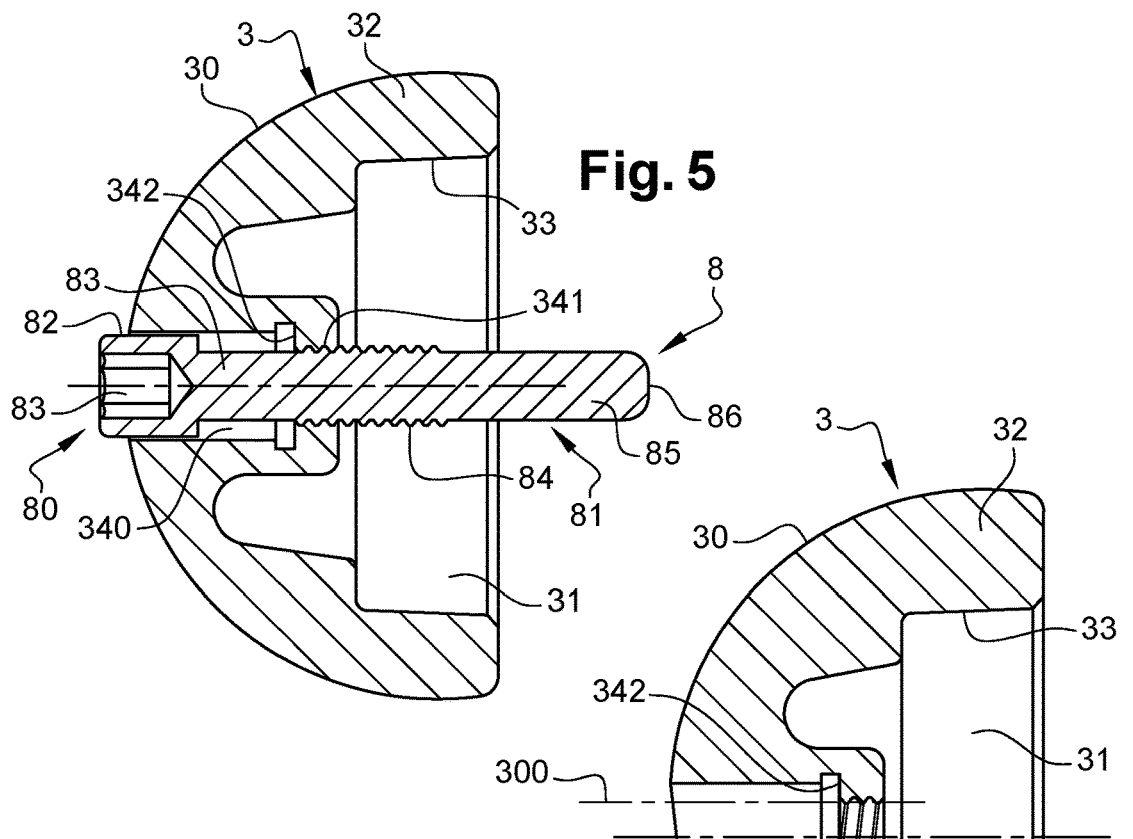
FIG. 5 is a schematic cross-sectional view of the glenosphere with the locking screw screwed in the standby position for the glenoid implant of FIG. 1.
Figure 11:
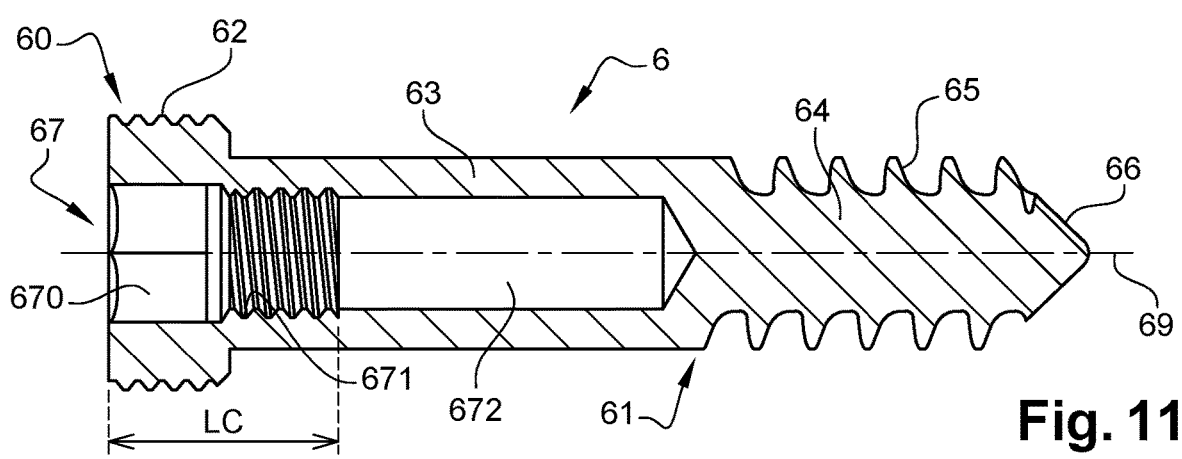
Figure 12:
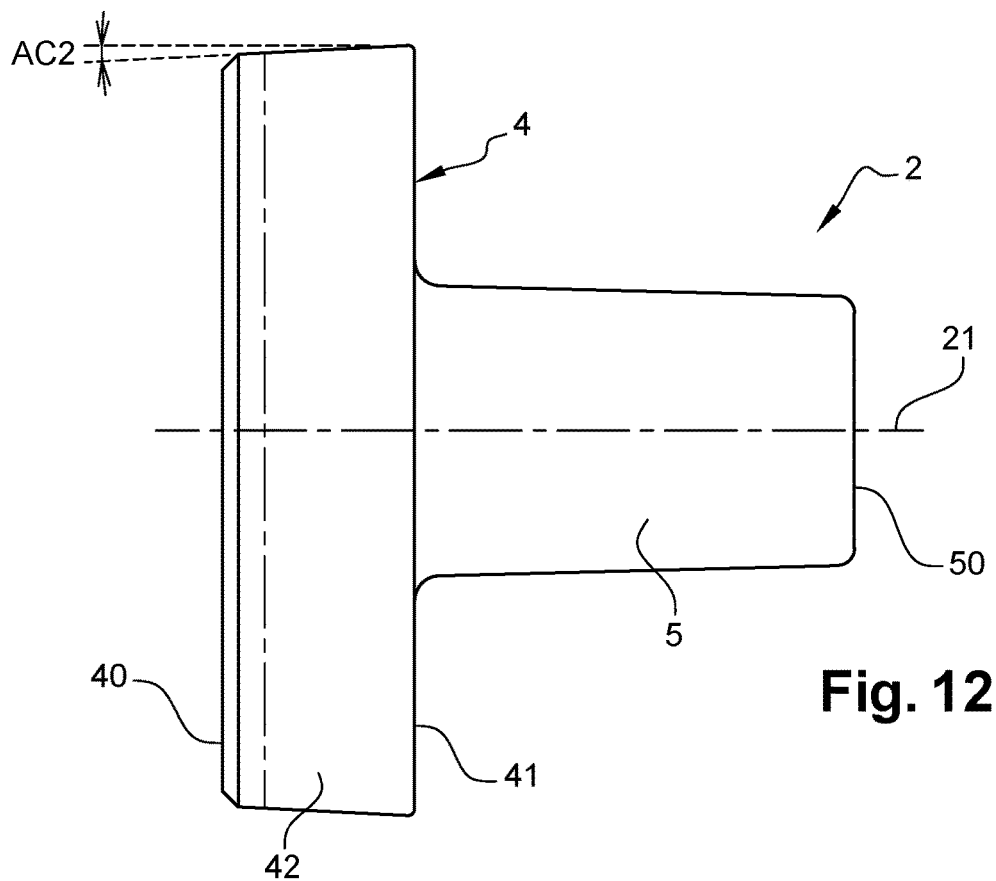
Figure 13:
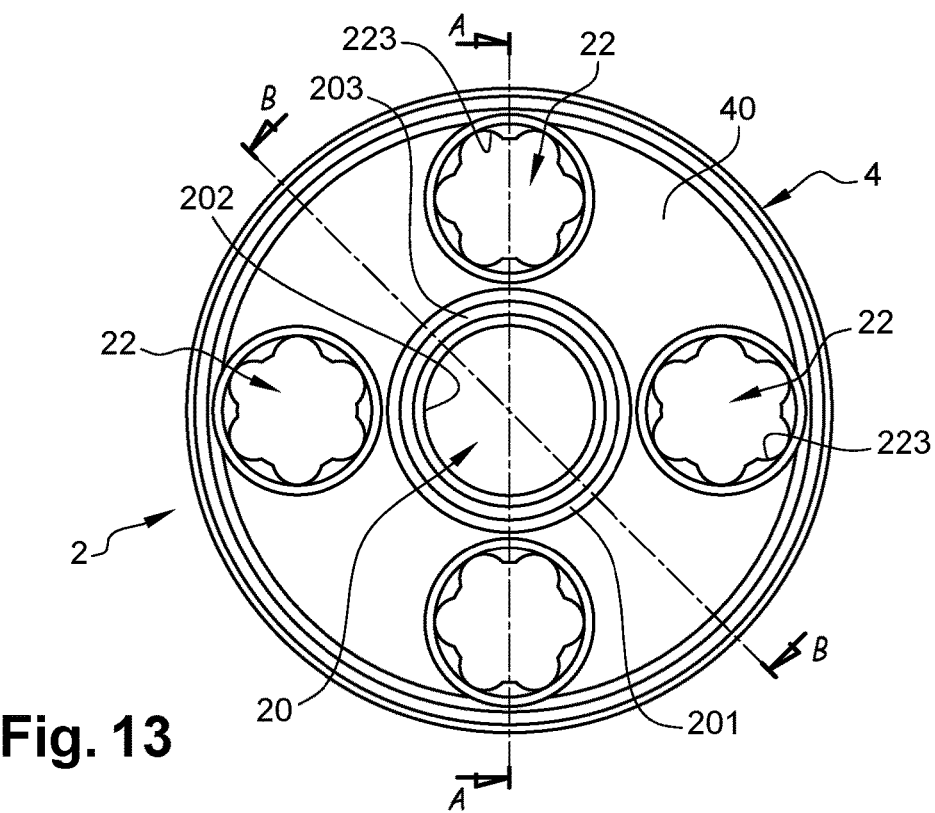
Figure 14:
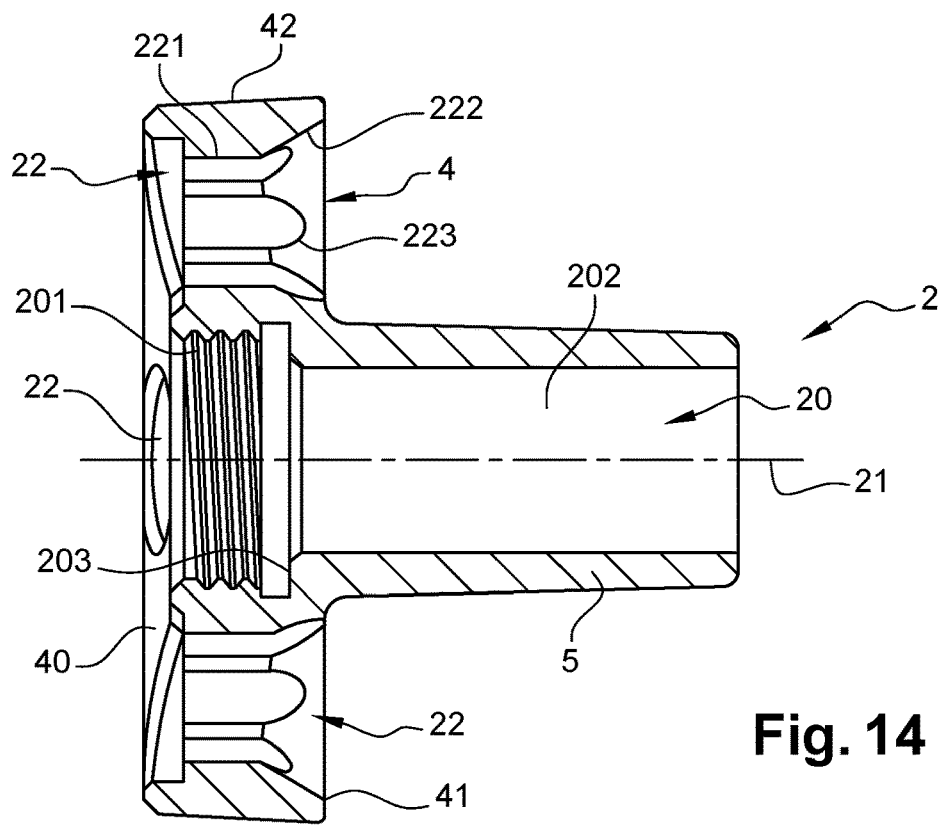
Figure 15:
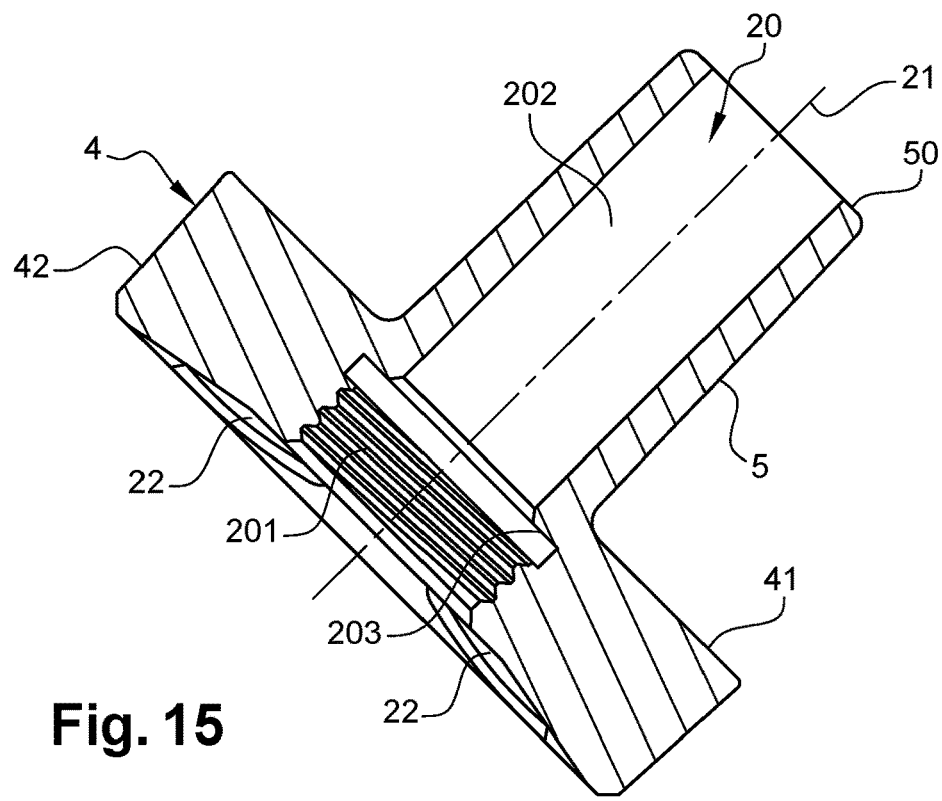
Figure 19:
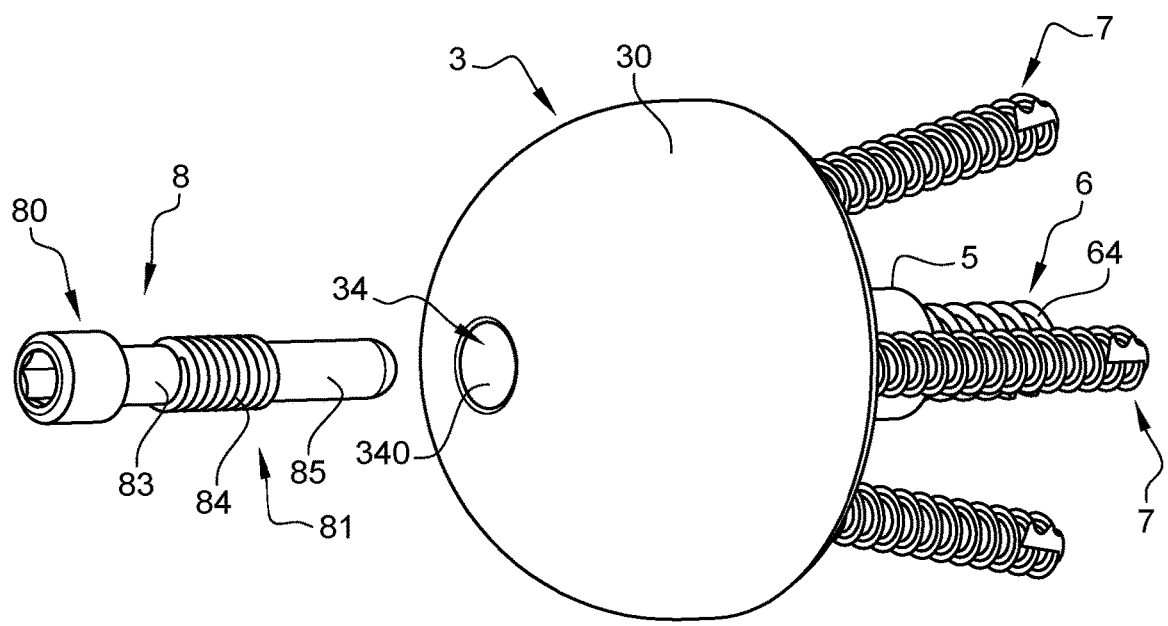
Figure 20:
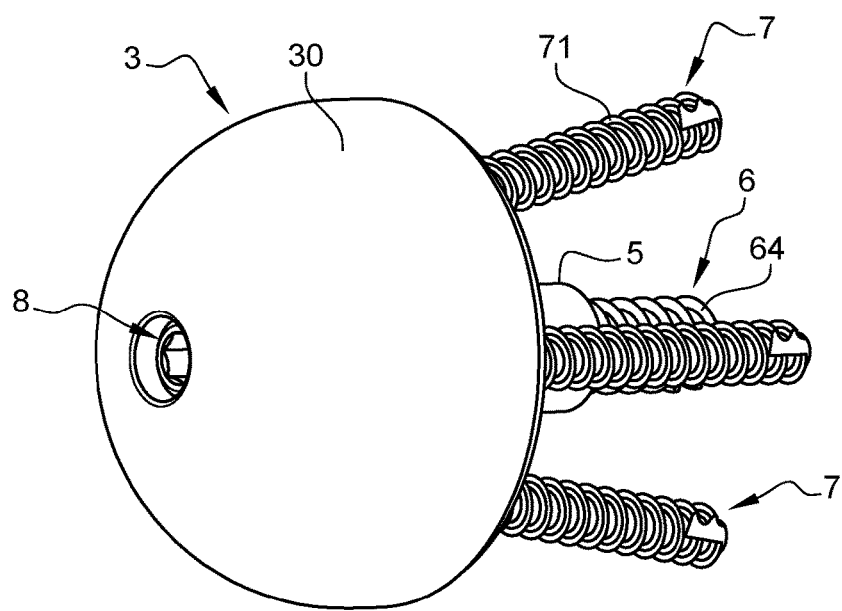
Figure 21:
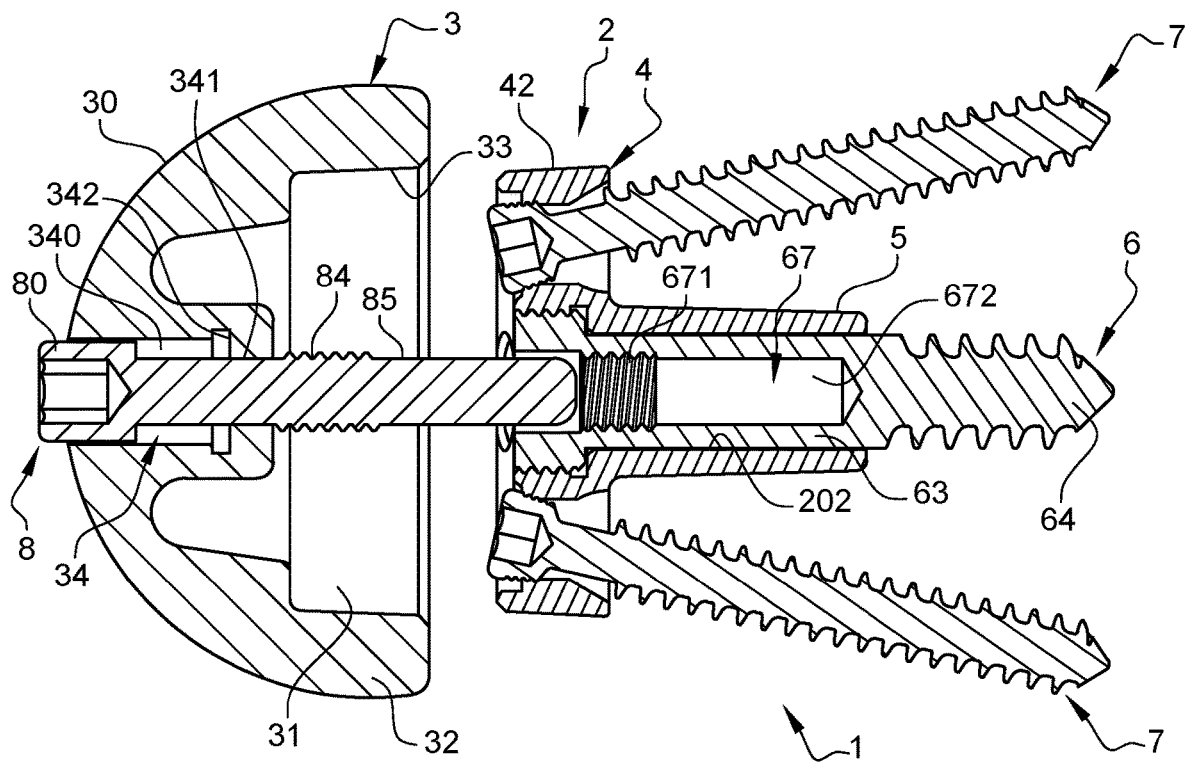
Figure 22:
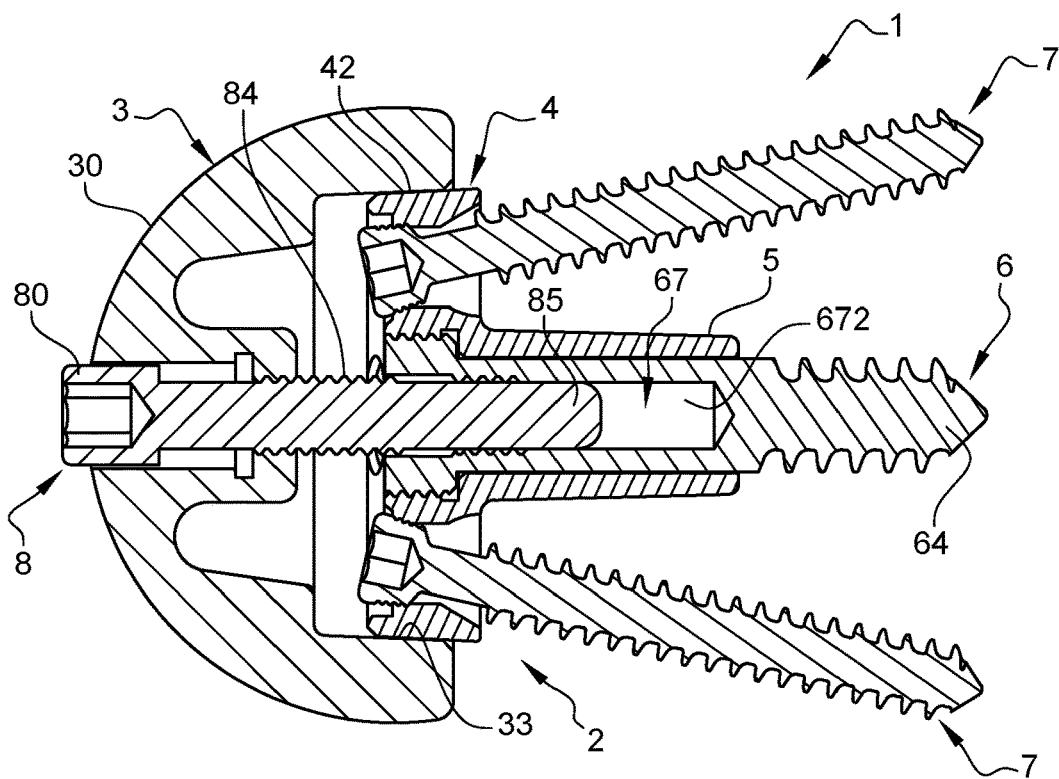
Figure 23:
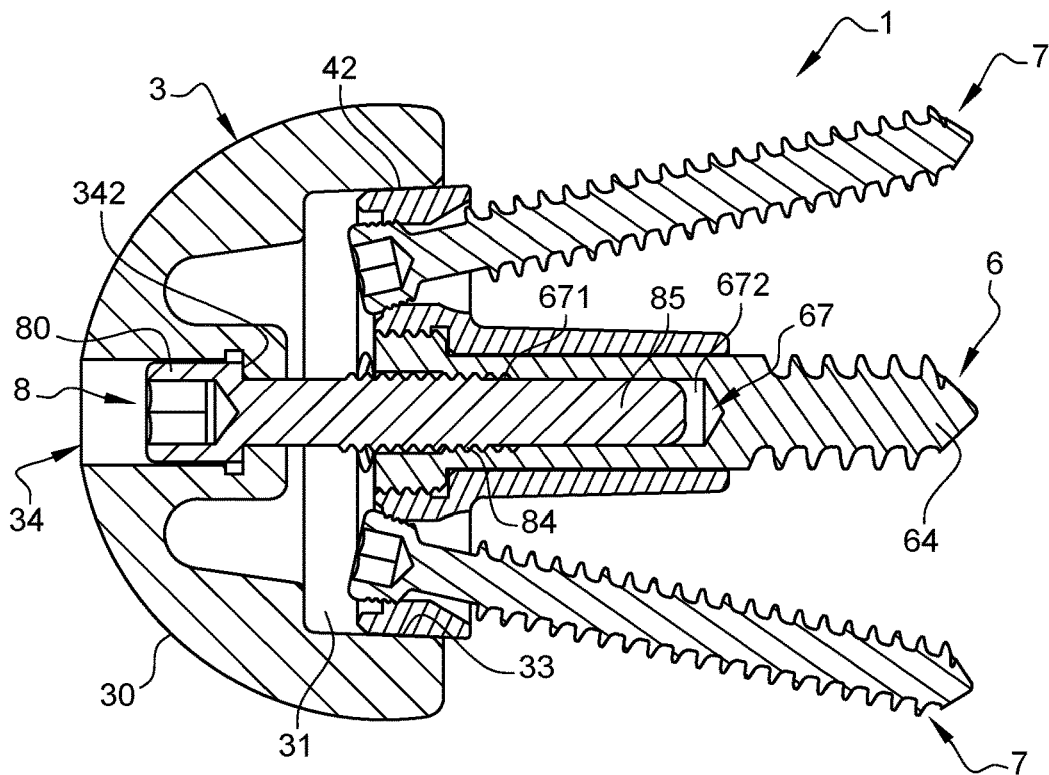

FIG. 11 a schematic cross-sectional view of the main anchoring screw of the glenoid implant of FIG. 1;

FIG. 12 is a schematic side view of the base of the glenoid implant of FIG. 1;

FIG. 13 is a schematic top view of the base of the glenoid implant of FIG. 1;

FIG. 14 is a schematic cross-sectional view of the base of the glenoid implant according to the sectional plane A-A of FIG. 13;

FIG. 15 is a schematic cross-sectional view of the base of the glenoid implant according to the sectional plane B-B of FIG. 13;

FIGS. 16 to 20 are schematic perspective views of the glenoid implant of FIG. 1 at different mounting steps; and FIGS. 21 to 23 are schematic cross-sectional views of the glenoid implant of FIG. 1 at different mounting steps.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Referring to FIG. 1, a glenoid implant 1 in accordance with the present disclosure, intended for an inverted shoulder prosthesis, comprises a base 2 and a glenosphere 3.

With further reference to FIGS. 12 to 15, the base 2 is intended to be anchored on a glenoid cavity of a scapula. This base 2 is an integral part made of a metallic material. The base 2 comprises a subplate 4 and a central stud 5.

The subplate 4 has:

an outer face 40 opposite the glenosphere 3, an inner face 41 opposite to the glenosphere 3 and intended to bear on the glenoid cavity, and in particular on the resected surface of the glenoid cavity; and a conical peripheral face 42 forming a male conical bearing surface for assembly with the glenosphere 3.

The peripheral face 42 has a taper angle AC2 comprised between 4 and 7 degrees, and in particular between 5 and 6 degrees, and forms a Morse taper.

The central stud 5 is an anchor stud intended to be anchored into the glenoid cavity, and this central stud 5 projects from the inner face 41 of the subplate 4. This central stud 5 is hollow and is thus in the form of a tubular sleeve, and it has a conical peripheral surface. The central stud 5 has a free tip 50.

The base 2 has a main orifice 20 crossing the base 2, wherein this main orifice 20 opens into the outer face 40 of the subplate 4 and crosses the subplate 4 throughout the thickness thereof and also crosses the central stud 5 so as to open into its tip 50. The main orifice 20 is centered on a central axis 21. The central stud 5 is also centered on this same central axis 21, and has in particular a rotational symmetry centered on this same central axis 21.

The main orifice 20 has successively, starting from the outer face 40 and in the direction of the tip 50:

an inlet portion 201 provided with a threading and opening onto the outer face 40;

a cylindrical and non-threaded (for example smooth) outlet portion 202 opening onto the tip 50, wherein this outlet portion 202 extends at least over the entire length of the central stud 5.

The outlet portion 202 has a reduced diameter in comparison with the inlet portion 201, so that the main orifice 20 has an annular bearing surface 203 between the end of the threading of the inlet portion 201 and the beginning of the outlet portion 202.

The glenoid implant 1 further comprises a main anchoring screw 6 intended to cross the main orifice 20 of the base 2, and event to be fastened inside this main orifice 20 and to open from the base 2 in order to provide a main anchorage of the base 2 and therefore of the glenoid implant 1 into the glenoid cavity.

Figure 10:
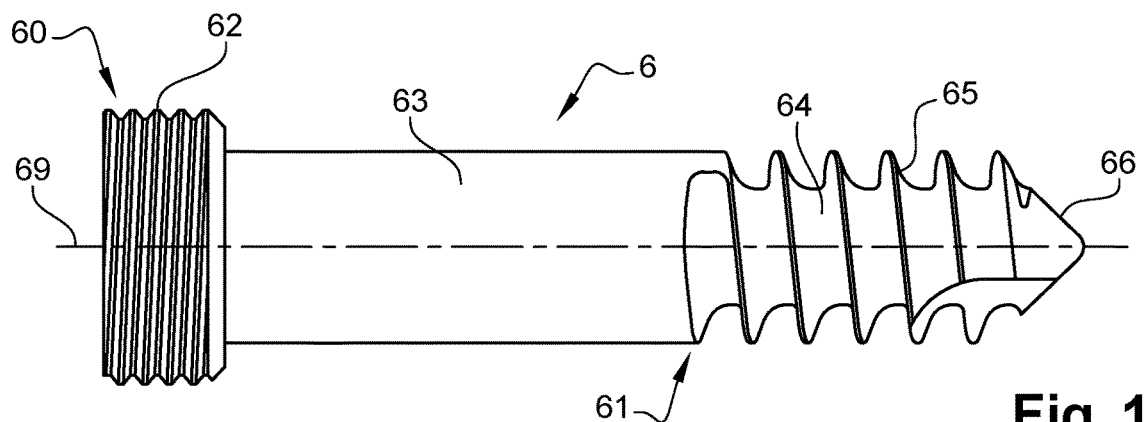
FIG. 10 is a schematic side view of the main anchoring screw of the glenoid implant of FIG. 1.

With further reference to FIGS. 10 and 11, the main anchoring screw 6 comprises a main head 60 and an anchor rod 61 centered on a longitudinal axis 69.

The main head 60 is an enlarged head which has an external tapping 62 which is complementary to the threading of the inlet portion 201 of the main orifice 20, so that this main head 60 could be screwed into this inlet portion 201 until abutting on the annular bearing surface 203 in a locked position shown in FIGS. 21 to 23.

Moreover, and as shown in FIGS. 21 to 23 and 17 and 18, once the main anchoring screw 6 is in place, the main head 60 does not extend beyond the outer face 40 of the subplate 4 of the base 2. The main head 60 is even flush with this outer face 40 of the subplate 4. Thus, the main anchoring screw 6 does not hinder the operations of screwing the secondary anchoring screws 7 described later on.

The anchor rod 61 has successively, starting from the main head 60:

a cylindrical and non-threaded (for example externally smooth) intermediate segment 63; and an end segment 64 provided with an external tapping 65 and which terminates in a pointed free end 66.

The intermediate segment 63 is intended to be slidably and tightly mounted inside the outlet portion 202 of the main orifice 20 of the base 2. Thus, the intermediate segment 63 has an outer diameter substantially equivalent to the inner diameter of the outlet portion 202, within mounting tolerances.

In turn, the end segment 64 is intended to extend beyond the tip 50 of the central stud 5 in order to be anchored into the glenoid cavity.

The external tapping 62 of the main head 60 has a tapping pitch smaller than that of the external tapping 65 of the end segment 64 of the anchor rod 61. The external tapping 62 is adapted for hooking in cancellous bone, and may have a tapping pitch in the range of 2 millimeters, whereas the external tapping 62 of the main head 60 has a metric tapping pitch, such as a for example a M10 tapping with a 1.5 millimeter pitch.

The main anchoring screw 6 also has an inner blind hole 67 opening into the main head 60 and stopping substantially at the level of the end of the intermediate segment 63.

This inner hole 67 is centered on the longitudinal axis 69 and it has successively, starting from the main head 60 and in the direction of the end segment 64 of the anchor rod 61:

an inlet portion 670 shaped so as to cooperate with a screwing tool, such an inlet portion 670 may for example have a polygonal section and in particular a hexagonal section so as to cooperate with a hex key;

an intermediate portion 671 provided with a threading; and a cylindrical and non-threaded (for example smooth) tip portion 672.

The base 2 has secondary orifices 22 disposed at the periphery thereof, around the main orifice 20, wherein these secondary orifices 22 cross the subplate 4 throughout the thickness thereof and open into the outer face 40 and into the inner face 41 at the periphery of the central stud 5. In the illustrated example, the secondary orifices 22 are four in number and are angularly distributed every 90 degrees.

Each secondary orifice 22 has successively, starting from the outer face 40 and in the direction of the inner face 41:

an inlet portion 221 provided with a threading and opening onto the outer face 40, wherein axial grooves 223 are formed in the inlet portion 221 by forming disrupted threads; and a flared and conical shaped outlet portion 222.

The glenoid 1 further comprises a plurality of secondary anchoring screws 7 intended to cross the secondary orifices 22 of the base 2, and even to be fastened inside these secondary orifices 22 and to open from the subplate 4 in order to provide a secondary anchorage of the base 2 and therefore of the glenoid implant 1 into glenoid cavity.

Each secondary anchoring screw 7 comprises a secondary head 70 and an anchor rod 71 which projects beyond the subplate 4 in order to be anchored into the glenoid cavity.

The secondary head 70 is an enlarged head which has an external tapping 72 which is complementary to the threading of the inlet portion 221 of the secondary orifice 22, so that this secondary head 70 could be screwed into this inlet portion 221. The secondary head 70 has a cupola-like shape which allows, together with the axial grooves 223, setting the inclination of the anchor rod 71.

The glenosphere 3 defines a convex articulation surface 30 formed as a spherical portion which is intended to articulate on a concave articulation surface of a hemispherical cap of a humeral implant intended to be anchored on a humerus.

This glenosphere 3 has a main cavity 31 open on the bottom opposite the base 2, wherein this main cavity 31 is delimited by a peripheral inner face 33 of a peripheral wall 32, wherein this peripheral inner face 33 forms a female conical bearing surface for assembly with the base 2.

More specifically, the glenosphere 3 is mounted on the base 2 according to a Morse taper mounting, by a mutual wedging between:

the peripheral face 42 of the subplate 4 of the base 2 forming a male conical bearing surface; and the peripheral inner face 33 of the glenosphere 3 forming a female conical bearing surface.

Thus, the peripheral inner face 33 has a taper angle AC3 equivalent to the taper angle AC2 of the peripheral face 42.

The glenosphere 3 further has a central orifice 34 crossing the glenosphere 3 and opening, on one side, into the convex articulation surface 30 and, on the other side, into the main cavity 31.

This central orifice 34 is centered on a central axis 35 which is coaxial with the conical peripheral inner face 33. In other words, the conical peripheral inner face 33 is centered on an axis of revolution which is coincident or coaxial with this central axis 35.

Figure 6:
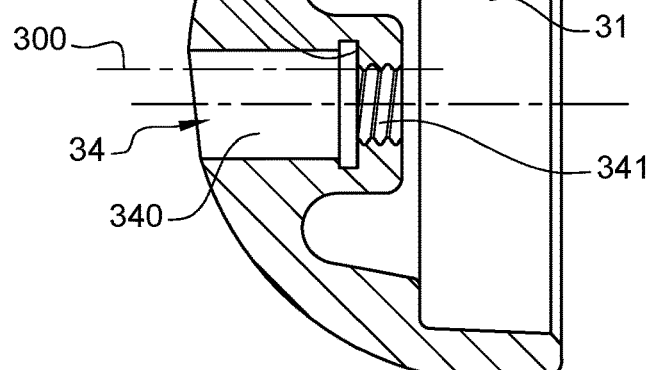
FIG. 6 is a cross-sectional view of a variant of the glenosphere with an offset of its central orifice with respect to the axis of revolution of the convex articulation surfaces formed as a spherical portion according to the present disclosure.
Figure 7:
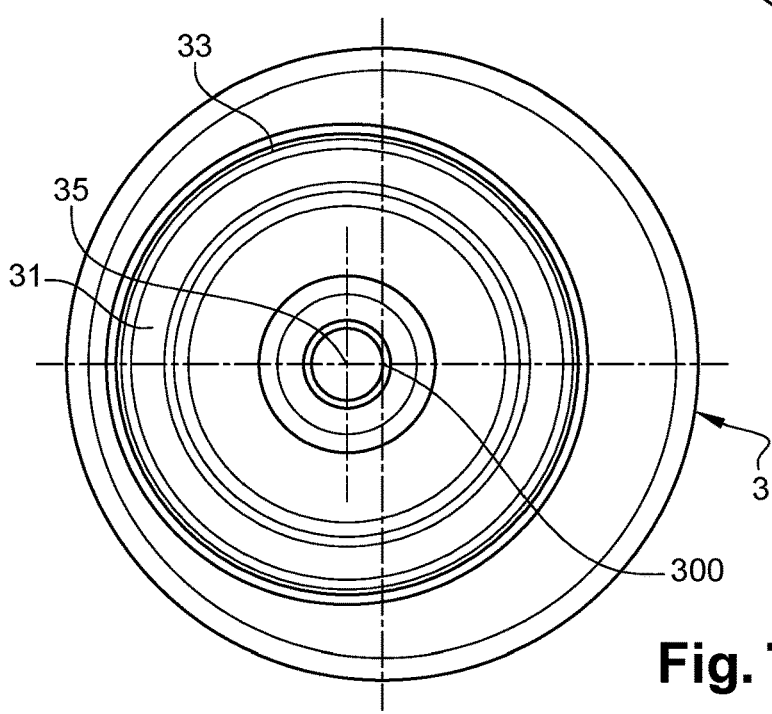
FIG. 7 is a bottom view of a variant of the glenosphere with an offset of its central orifice with respect to the axis of revolution of the convex articulation surfaces formed as a spherical portion according to the present disclosure.

In the example of FIGS. 2 to 5, this central axis 35 is also coincident with the axis of revolution of the convex articulation surface 30, whereas in the example of FIGS. 6 and 7, this central axis 35 is offset and parallel relative to the axis of revolution 300 of the convex articulation surface 30.

The central orifice 34 has successively, starting from the convex articulation surface 30 in the direction of the main cavity 31 (and therefore in the direction of the base 2):

a cylindrical and non-threaded (for example smooth) proximal portion 340 opening into the convex articulation surface 30; and a distal portion 341 provided with a threading and opening into the main cavity 31.

The distal portion 341 has a reduced diameter in comparison with the proximal portion 340, so that the central orifice 34 has an annular bearing surface 342 between the end of the proximal portion 340 and the beginning of the threading of the distal portion 341.

The glenoid implant 1 further comprises a locking screw 8 intended to cross the central orifice 34 of the glenosphere 3 in order to:

guide the glenosphere 3 on the base 2 so as to make the peripheral inner face 33 and the peripheral face 42 of the subplate 4 cooperate for a Morse taper mounting; and lock the glenosphere 3 on the base 2 in a locked position.

Figure 8:
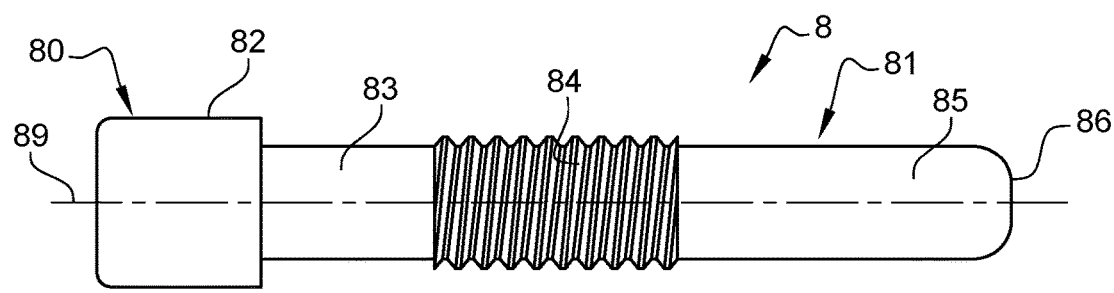
FIG. 8 is a schematic side view of the locking screw of the glenoid implant of FIG. 1.
Figure 9:
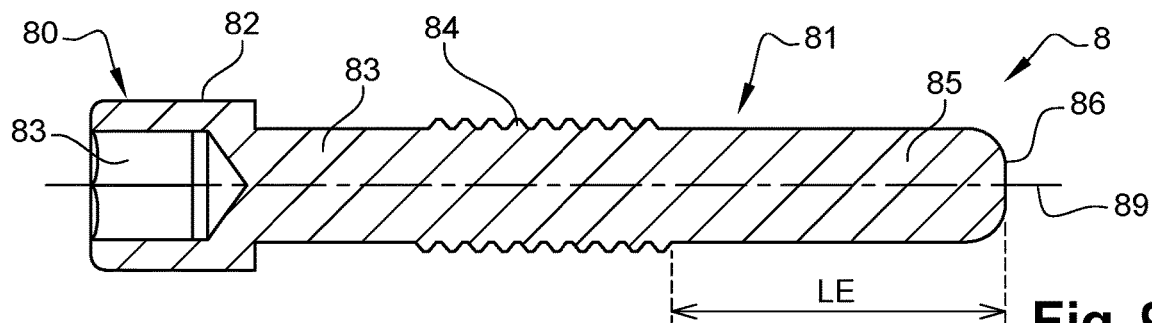
FIG. 9 is a schematic cross-sectional view of the locking screw of the glenoid implant of FIG. 1.

With further reference to FIGS. 8 and 9, the locking screw 8 comprises a proximal head 80 and a locking rod 81 centered on a longitudinal axis 89. When in place, the locking screw 8 is coaxial with the main anchoring screw 6, in other words the longitudinal axis 89 and the longitudinal axis 69 are coaxial or coincident.

The proximal head 80 has a cylindrical and non-tapped (for example smooth) outer peripheral face 82, whose outer diameter is substantially equivalent (within mounting tolerances) to the inner diameter of the proximal portion 340 of the central orifice 34 so that this proximal head 80 could be guided and tightly mounted inside this proximal portion 340. The proximal portion 340 shaped so as to completely receive the proximal head 80 so that the latter does not project from the convex articulation surface 30.

The proximal head 80 also has a blind hole 87 is shaped so as to cooperate with a screwing tool, such a blind hole 87 may for example have a polygonal section and in particular a hexagonal section so as to cooperate with a hex key.

The locking rod 81 has successively, starting from the proximal head 80:

a cylindrical and non-threaded (for example smooth) proximal segment 83;

an intermediate segment 84 provided with an external tapping which is complementary to both the threading of the intermediate portion 671 of the inner hole 67 of the main anchoring screw 6 and the threading of the distal portion 341 of the central orifice 34 of the glenosphere 3; and a cylindrical and non-threaded (for example smooth) end segment 85 which terminates in a free end 86.

The end segment 85 has a length LE which is larger than the cumulated length LC of the inlet portion 670 and of the intermediate portion 671 of the inner hole 67 of the main anchoring screw 6, so that this end segment 85 is intended to slide inside the tip portion 672 of the inner hole 67 of the main anchoring screw 6. Furthermore, the end segment 85 has an outer diameter substantially equivalent (within mounting tolerances) to the inner diameter of the tip portion 672 of the inner hole 67 so that this end segment 85 could be guided and tightly mounted inside this tip portion 672.

Thus, by sliding inside the tip portion 672 of the inner hole 67, the end segment 85 allows centering the conical bearing surfaces (i.e. the peripheral inner face 33 and the peripheral face 42) relative to one another, then the intermediate segment 84 cooperates by screwing with the intermediate portion 671 of the inner hole 67 of the main anchoring screw 6 to lock the mutual wedging of the conical bearing surfaces 33, 42 until the proximal head 80 of the locking screw 8 abuts on the annular bearing surface 342 provided inside the central orifice 34 of the glenosphere 3.

It should be noted that the distal portion 341 of the central orifice 34 of the glenosphere 3 has a length smaller than a length of the intermediate segment 84 if the locking rod 81 of the locking screw 8, and also smaller than a length of the proximal segment 83 of the locking rod 81.

The following description covers the method of use of a glenoid implant 1 as described hereinabove.

Figure 16:
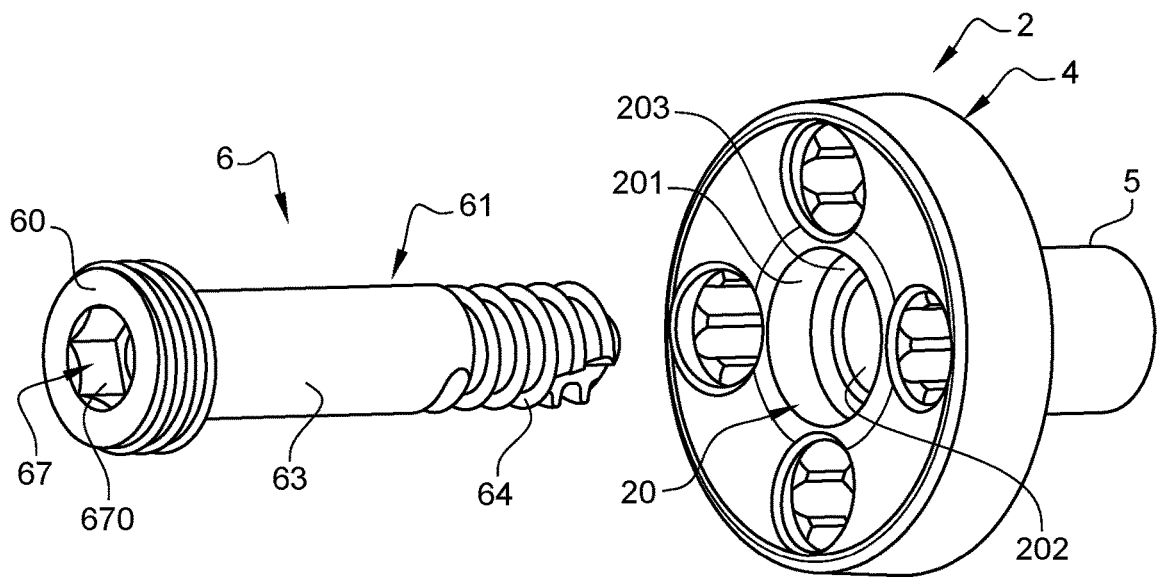

In a first step illustrated in FIG. 16, the main anchoring screw 6 is fitted into the main orifice 20 of the base 2, until the main head 60 is screwed into the inlet portion 201 of the main orifice 20 until abutting on the annular bearing surface 203 in a locked position shown in FIGS. 21 to 23.

Figure 17:
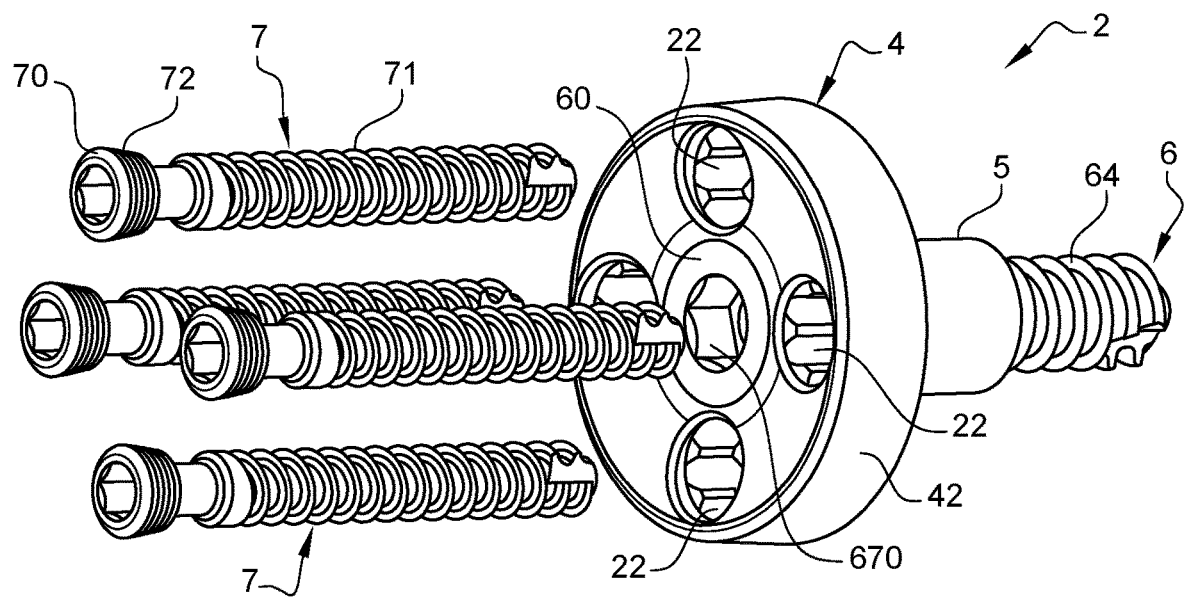

In a second step illustrated in FIG. 17, the main anchoring screws 6 are fitted into the secondary orifices 22 of the base 2, until the secondary heads 70 are screwed into the inlet portions 221 of the secondary orifices 22.

In a third step illustrated in FIG. 21, the locking screw 8 is fitted into the central orifice 34 of the glenosphere 3 until the intermediate segment 84 comes into the distal portion 341 of the central orifice 34, and then the locking screw 8 is screwed until the intermediate segment 84 projects beyond the distal portion 341 so that the end segment 85 of the locking rod 81 projects beyond the glenosphere 3 out of the main cavity 31.

In this manner, the locking screw 8 is blocked in the central orifice 34 of the glenosphere 3.

Figure 18:
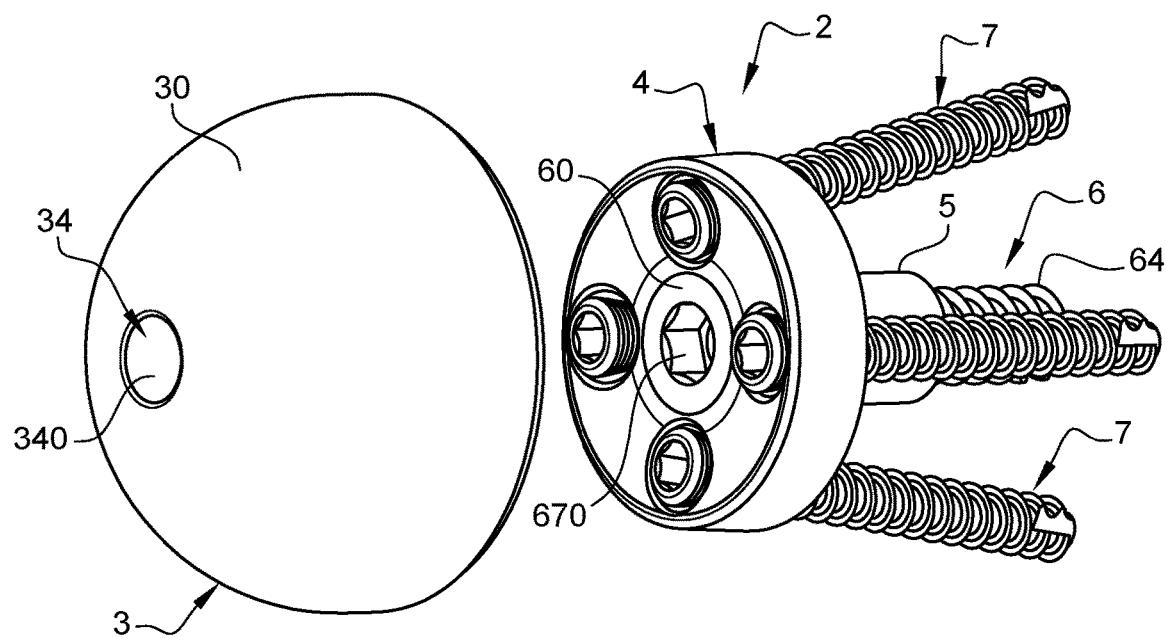

This third step may be performed after having positioned the glenosphere 3 on the base 2, as illustrated in FIGS. 18 to 20.

In a fourth step (which may precede or follow the third step) illustrated in FIG. 22, the glenosphere 3 is brought close to and mounted on the base 2 so that:

the female and male conical bearing surfaces (i.e. the peripheral inner face 33 and the peripheral face 42) are brought into contact with one another; and the end segment 85 of the locking rod 81 passes through the inlet portion 670 and the intermediate portion 671 of the inner hole 67 of the main anchoring screw 6 so as to slide inside the tip portion 672 of the inner hole 67, thereby providing a centering for the female and male conical bearing surfaces 33, 42.

At this level, the proximal head 80 of the locking screw 8 is away from the from the annular bearing surface 342 provided inside the central orifice 34 of the glenosphere 3, which enables an impingement on the glenosphere 3.

Thus, in a fifth step, the glenosphere 3 is impinged so as to provide a stable and reliable mutual wedging between the female and male conical bearing surfaces 33, 42.

Finally, in a fifth step illustrated in FIG. 23, the locking rod 81 is pushed in until the intermediate segment 84 comes into the intermediate portion 671 of the inner hole 67 of the main anchoring screw 6, and then the locking screw 8 is screwed so that this intermediate segment 84 cooperates by screwing with this intermediate portion 671 of the inner hole 67 of the main anchoring screw 6 until the proximal head 80 of the locking screw 8 abuts on the annular bearing surface 342 provided inside the central orifice 34 of the glenosphere 3. During this screwing, the end segment 85 of the locking rod 81 continues sliding inside the tip portion 672 of the inner hole 67.

In the end, the locking screw 8 provides locking of the mutual wedging of the female and male conical bearing surfaces 33, 42, bearing in mind that the subplate 4 extends at least partially inside the main cavity 31 of the glenosphere 3.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, material, manufacturing, and assembly tolerances, and testing capability.

As used herein, the phrase at least one of A, B, and C should be construed to mean a logical (A OR B OR C), using a non-exclusive logical OR, and should not be construed to mean "at least one of A, at least one of B, and at least one of C."

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A glenoid implant for an inverted shoulder prosthesis comprising:
   a base configured to be anchored on a glenoid cavity of a scapula and having a main orifice extends through the base;
   a glenosphere defining a convex articulation surface formed in a hemisphere portion and having a central orifice passing through the glenosphere, wherein the glenosphere is mounted on the base by mutual wedging between a female conical bearing surface on the glenosphere and a male conical bearing surface on the base;
   a main anchoring screw passing through the main orifice of the base and shaped for anchorage of the base on the glenoid cavity, wherein the main anchoring screw comprises a main head and an anchor rod having an end segment with an external tapping; and
   a locking screw, coaxial with the main anchoring screw, passing through the central orifice of the glenosphere to lock the glenosphere on the base in a locked position, wherein the locking screw comprises a proximal head and a locking rod having an intermediate segment with an external tapping and extended by an end segment, wherein:
   the main anchoring screw has an inner hole opening into the main head and having successively, starting from the main head and in a direction of the end segment of the anchor rod, an inlet portion shaped to cooperate with a screwing tool, an intermediate portion including a threading and a tip portion, and
   the end segment of the locking rod has a length longer than a cumulated length of the inlet portion and of the intermediate portion of the inner hole of the main anchoring screw to slide inside the tip portion of the inner hole of the main anchoring screw to center the female and male conical bearing surfaces relative to one another, and the intermediate segment of the locking rod is adapted to be threadably engaged to the intermediate portion of the inner hole of the main anchoring screw to lock mutual wedging of the female and male conical bearing surfaces, the proximal head of the locking screw abutting on an annular bearing surface inside the central orifice of the glenosphere,
   the central orifice of the glenosphere has successively, starting from the convex articulation surface in the direction of the base, a proximal portion shaped to receive the proximal head of the locking screw, and a distal portion having threading complementary to the external tapping of the intermediate segment of the locking rod of the locking screw, wherein the annular bearing surface of the central orifice of the glenosphere is at an interface between the proximal portion and the distal portion.

2. The glenoid implant according to claim 1, wherein the distal portion of the central orifice of the glenosphere has a length smaller than a length of the intermediate segment of the locking rod of the locking screw.

3. The glenoid implant according to claim 1, wherein the distal portion of the central orifice of the glenosphere has a length smaller than a length of a proximal segment of the locking rod of the locking screw.

4. The glenoid implant according to claim 1, wherein the locking rod of the locking screw has a proximal segment extending between the proximal head and the intermediate segment.

5. The glenoid implant according to claim 1, wherein the main anchoring screw and the locking screw are coaxial with the female and male conical bearing surfaces.

6. The glenoid implant according to claim 1, wherein, in the locked position, the main head of the main anchoring screw abuts on an annular bearing surface inside the main orifice of the base.

7. The glenoid implant according to claim 1, wherein the main head of the main anchoring screw has an external tapping, and the main orifice of the base has an inlet portion opening onto an outer face of the base opposite the glenosphere, wherein the inlet portion includes a threading complementary to the external tapping of the main head, so that the main head is screwed into the inlet portion.

8. The glenoid implant according to claim 7, wherein the external tapping of the main head of the main anchoring screw has a tapping pitch smaller than that of the external tapping of the end segment of the anchor rod.

9. The glenoid implant according to claim 7, wherein the main orifice of the base has an outlet portion which extends the inlet portion and which extends through a central stud of the base, and the anchor rod has an intermediate segment shaped so as to be mounted inside the outlet portion of the main orifice of the base.

10. The glenoid implant according to claim 1, wherein the base has a central stud projecting from an inner face opposite to the glenosphere, wherein the central stud is hollow and the main orifice extends through the central stud and the end segment of the anchor rod projects beyond the central stud.

11. The glenoid implant according to claim 1 further comprising a plurality of secondary anchoring screws shaped for anchorage of the base on the glenoid cavity, wherein the plurality of secondary anchoring screws pass through the base and are disposed at a periphery around the main anchoring screw.

12. The glenoid implant according to claim 1, wherein the main head of the main anchoring screw does not project beyond an outer face opposite the glenosphere.

\* \* \* \* \*